US006258350B1

(12) United States Patent
Mallick

(10) Patent No.: US 6,258,350 B1
(45) Date of Patent: Jul. 10, 2001

(54) SUSTAINED RELEASE OPHTHALMIC FORMULATION

(75) Inventor: Sushanta Mallick, Dallas, TX (US)

(73) Assignee: Alcon Manufacturing, Ltd., Fort Worth, TX (US)

(*) Notice: Subject to any disclaimer, the term of this patent is extended or adjusted under 35 U.S.C. 154(b) by 0 days.

(21) Appl. No.: 09/456,617

(22) Filed: Dec. 8, 1999

Related U.S. Application Data

(60) Provisional application No. 60/116,487, filed on Jan. 20, 1999.

(51) Int. Cl.$^7$ .............................. A61K 9/10; A61K 47/32

(52) U.S. Cl. ......................................... 424/78.04

(58) Field of Search ........................................ 424/78.04

(56) References Cited

U.S. PATENT DOCUMENTS

| | | | |
|---|---|---|---|
| 2,774,789 | 12/1956 | Tullar | 260/570.6 |
| 3,202,660 | 8/1965 | Zeile et al. | 260/254 |
| 3,309,406 | 3/1967 | Kunz et al. | 260/570.7 |
| 3,619,370 | 11/1971 | Weinstock | 260/247.1 |
| 3,655,663 | 4/1972 | Wasson | 260/247.1 |
| 3,657,237 | 4/1972 | Weinstock | 260/247.1 |
| 3,663,607 | 5/1972 | Barrett | 260/501.1 |
| 3,836,671 | 9/1974 | Barrett et al. | 424/324 |
| 3,857,952 | 12/1974 | Wooldridge et al. | 424/324 |
| 3,867,519 | 2/1975 | Michaels | 424/19 |
| 3,962,414 | 6/1976 | Michaels | 424/19 |
| 3,987,163 | 10/1976 | Rankin | 424/78 |
| 4,012,444 | 3/1977 | Lunts et al. | 260/559 |
| 4,127,674 | 11/1978 | Leopold | 424/324 |
| 4,207,890 | 6/1980 | Mamajek et al. | 128/223 |
| 4,252,984 | 2/1981 | Manoury et al. | 564/349 |
| 4,271,143 | 6/1981 | Schoenwald et al. | 424/78 |
| 4,407,792 | 10/1983 | Schoenwald et al. | 424/81 |
| 4,462,982 | 7/1984 | Samejima et al. | 424/35 |
| 4,521,414 | 6/1985 | Chiou et al. | 514/229 |
| 4,694,022 | 9/1987 | Gerson et al. | 514/554 |
| 4,859,462 | 8/1989 | Chow et al. | 424/79 |
| 4,911,920 | 3/1990 | Jani et al. | 424/78 |

(List continued on next page.)

FOREIGN PATENT DOCUMENTS

| 0 429 732 A1 | 6/1991 | (EP) . |
|---|---|---|
| 2 130 585 A | 6/1984 | (GB) . |
| WO 89/06964 | 8/1989 | (WO) . |

OTHER PUBLICATIONS

Stalker et al., "Enhancement of Ocular Drug Bioavailability Through the Use of Drug–Resin Complexes I: Tear Film Concentrations Versus Time Profiles for Pencillin–G," Abstract of Papers Presented Before the American Pharmaceutical Association Academy of Pharmaceutical Sciences 33$^{rd}$ National Meeting, Sand Diego, CA; vol. 12 (2), p. 116, No. 57 (1982).

Stalker et al., "Enhancement of Ocular Drug Bioavailability Through the Use of Drug–Resin Complexes II: Aqueous Humor Concentrations Versus Time Profiles for Nafcillin," Abstract of Papers Presented Before the American Pharmaceutical Association Academy of Pharmaceutical Sciences 33$^{rd}$ National Meeting, San Diego, CA: vol. 12 (2), p. 116, No. 58 (1982).

Rohm and Hass Product Brochure for Amberlite® and Duolite® (1991).

Schoenwald et al., "Influence of High–Viscosity Vehicles on Miotic Effect of Pilocarpine," *J. of Pharm. Sciences*, vol. 67(9), pp. 1280–1283 (1978).

Stallker "Enhancement of Ocular Drug Bioavailability Through the Use of Micronized, Functionalized Polymers as Carriers of Therapeutic Agents," Dissertation submitted at the University of Kentucky (1983).

Machin et al., "$\beta_1$–Selective Adrenoceptor Antagonists. 2. 4–Ether–Linker Phenoxypropanolamines," *J.Med. Chem.*, vol. 26, pp. 1570–1576 (1983).

McClure et al., "Antihypertensive –β–Adrenergic Blocking Agents: N–Aralkyl analogues of 2–[3–(tert–Butylamino)–2–hydroxypropoxy]–3–cyanopyridine$^1$," *J. Med. Chem.*, vol. 26., pp. 649–657 (1983).

Pitha et al., "β–Adrenergic Antagonists with Multiple Pharmacophores: Persistent Blockade of Receptors," *J. Med. Chem.*, vol. 26, pp. 7–11 (1983).

Kierstead et al., "$\beta_1$–Selective Adrenoceptor Antagonists. 1. Synthesis and β–Adrenergic Blocking Activity of a Series of Binary (Aryloxy)propanolamines," *J. Med. Chem.*, vol. 26, pp. 1561–1569 (1983).

Large et al., "β–Adrenergic Blocking Agents," *J. Med. Chem.*, vol. 26, pp. 352–357 (1983).

Machin et al., "$\beta_1$–Selective Adrenoceptor Antagonists. 3. 4–Azolyl–Linked Phenoxypropanolamines," *J. Med. Chem.*, vol. 27, pp. 503–509 (1984).

Gennaro, A. *Remington's Pharmaceutical Sciences*, Mack Publishing Company, Easton, PA (1985) "How to Use Ophthalmic Ointment".

Heath et al., Adsorption of β–Adrenoceptor Antagonists to Amberlite® Resin, *Br. J. Clin. Pharmac.*, vol. 15, pp. 490–492 (1983).

Heyd, "Polymer–Drug Interaction: Stability of Aqueous Gels Containing Neomycin Sulfate," *J. of Pharm. Sciences*, vol. 60 (9), pp. 1343–1345 (1971).

Baldwin et al., "$\beta_1$–Selective Adrenoceptor Antagonists: Examples of the 2–[4–[3–(Substituted–amino)–2–hydroxypropoxy]phenyl]imidazole Class," *J. Med. Chem.*, vol. 26, pp. 950–957 (1983).

Erhardt et al., "Ultra–Short Acting β–Adrenergic Receptor Blocking Agents. 3. Ethylenediamine Derivatives of (Aryloxy)propanolamines Having Esters on the Aryl Function," *J. Med Chem.*, vol. 26, pp. 1109–1112 (1983).

*Primary Examiner*—Peter F. Kulkosky
(74) *Attorney, Agent, or Firm*—Patrick M. Ryan

(57) ABSTRACT

Sustained release formulations for topical ophthalmic administration are disclosed. The formulations comprise a basic active, a polyanionic polymer and a poly (styrenedivinyl) benzene cation exchange resin having a degree of cross-linking from about 4 to about 4.5%.

15 Claims, No Drawings

U.S. PATENT DOCUMENTS

| | | | |
|---|---|---|---|
| 4,983,392 | 1/1991 | Robinson | 424/427 |
| 5,188,826 | 2/1993 | Chandrasekaran et al. | 424/78.04 |
| 5,192,535 | 3/1993 | Davis et al. | 424/78.04 |
| 5,212,162 | 5/1993 | Missel et al. | 514/54 |
| 5,635,172 | 6/1997 | Jani et al. | 424/78.04 |
| 5,837,226 * | 11/1998 | Jungherr et al. | 424/78.04 |
| 5,948,401 * | 9/1999 | Donabedian et al. | 424/78.04 |

* cited by examiner

SUSTAINED RELEASE OPHTHALMIC FORMULATION

This application claims priority to U.S. Provisional Application, Ser. No. 60/116,487, filed Jan. 20, 1999.

BACKGROUND OF THE INVENTION

This invention relates to ophthalmic formulations of cationic, pharmaceutically active agents. The formulations of the present invention are characterized by sustained release of the active agent, and are initially and continually comfortable to the eye. Specifically, the invention relates to formulations of the above characteristics which comprise, inter alia, a basic active and certain cationic exchange resins (finely divided) dispersed in an aqueous solution or gel of an acidic mucomimetic polymer. Such formulations are characterized by controlled cationic-anionic interactions, which appear to be responsible for the resulting comfort and sustained release properties. This invention also relates to methods of treatment which comprise administering the described compositions to the eye.

U.S. Pat. No. 4,911,920, the entire contents of which are incorporated by reference, discloses sustained release formulations for glaucoma therapy, wherein the formulations comprise a basic active and a cationic exchange resin dispersed in an aqueous solution or gel of an acidic, mucomimetic polymer. The cationic-exchange resin in the '920 formulations can be "any pharmaceutical grade cationic exchange resin" (Col. 3, lines 65–66 of the '920 patent) and include the "Amberlite" (Rohm & Haas) and "Dowex" (Dow Chemical Co.) lines of commercially available resins. Examples 2 and 3 of the '920 patent disclose Amberlite IRP-69 resin, a sodium poly(styrenedivinyl benzene) sulfonate having an approximately 8% degree of cross-linking according to its product brochure.

SUMMARY OF THE INVENTION

The ophthalmic formulations of the present invention are in the form of pourable, aqueous dispersions and aqueous gels. The formulations comprise a polyanionic polymer, a poly(styrenedivinyl) benzene cation exchange resin having a degree of cross-linking from about 4 to about 4.5%, and a basic active.

The formulations of the present invention demonstrate sustained release of the basic active and are comfortable on topical administration to the eye. When basic actives are topically administered, a stinging sensation generally results. Achieving both comfort and sustained release permits administration of a class of compounds that otherwise might not be considered. The cationic exchange resins contained in the formulations of the present invention are an essential ingredient for both comfort and sustained release. These cationic exchange resins provide unexpectedly superior sustained release profiles compared to analogous, but more highly cross-linked, resins.

DETAILED DESCRIPTION OF THE INVENTION

The formulations of the present invention comprise, in addition to conventional ingredients which provide, for example, bacteriostatic and formulatory balance functions, a basic active, a polyanionic polymer and a poly(styrenedivinyl) benzene cation exchange resin having a degree of cross-linking from about 4 to about 4.5%.

Basic Active Component

As used herein, "basic active" means a positively-charged, ophthalmically acceptable active agent. Suitable basic actives include all presently known beta blockers which demonstrate the requisite cationic charge and act to reduce intraocular pressure. Typically, such beta blockers are represented by the following generic structure:

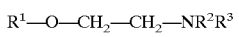

$$R^1\text{—}O\text{—}CH_2\text{—}CH_2\text{—}NR^2R^3$$

wherein:

$R^1$ is a substituted or unsubstituted cyclic or aliphatic moiety; cyclic moieties include mono- and polycyclic structures which may contain one or more heteroatoms selected from C, N, and O; $R^2$ and $R^3$ are independently selected from H and substituted and unsubstituted alkyl. With regard to Structure (I), above, the following references are incorporated herein by reference: *Annual Reports in Medicinal Chemistry* 14, 81–87 (1979); *J. Med. Chem.* 1983, 26, 1570–1576; ibid., 1984, 27, 503–509, ibid., 1983, 26, 7–11; ibid, 1983, 26, 1561–1569; ibid., 1983, 1109–1112; ibid., 1983, 26, 352–357. Representative of such basic actives are betaxolol, timolol, befunolol, labetalol, propanolol, bupranolol, metaprolol, bunalol, esmalol, pindolol, carteolol, hepunolol, metipranolol, celiprolol, azotimolol, diacetolol, acebutolol, salbutamol, atenulol, isoxaprolol, and the like.

Basic actives also include the following classes of drugs which are used in treatment of ocular hypertension and glaucoma: pilocarpine, epinephrine; proepinephrine, norepinephrine; pronorepinephrine, clonidine; and clonidine derivatives, for example, p-aminoclonidine, pacetoamidoclonidine and brimonidine.

Thus, in summary, the basic active component of the present invention is defined as an ophthalmically acceptable pharmaceutical active having a cationic nature in an aqueous medium in the pH range of from 3.0 to 8.5. The most preferred basic actives are betaxolol and timolol. The basic active is present at a level of from about 0.01 to 4.0 wt. %; the most preferred range is from 0.10 to 1.0 wt. %.

Polyanionic Polymer Component

The high molecular weight, polyanionic polymers useful in the present invention are ophthalmically acceptable and have a molecular weight of from about 50,000 to about 6 million. The polymers are characterized as having carboxylic acid functional groups, and preferably contain from 2 to 7 carbon atoms per functional group. Depending upon the identity and concentration of the polyanionic polymer, the compositions of the present invention may be in the form of a liquid or a gel.

Suitable anionic polymers useful in the present invention include carboxyl vinyl polymers. Preferred polymers include the so called carbomers, available under the trade name Carbopol from the B.F. Goodrich Company; and ethylene maleic anhydride polymeric material, available under the trade name EMA from the Monsanto Company. The known and readily available polymers Carbopol 934P, 940 and 974P are most preferred. The polymers are used in the aqueous gel compositions at a level up to about 8% by weight; pourable liquid compositions generally comprise about 0.05% to about 2.0% weight polymer.

Ion Exchange Resin

The cationic exchange resin component of the formulations of the present invention provides an additional means of sustained release of the basic active, and appears to be necessary for initial and prolonged comfort. Such resins are characterized as either strongly acidic such as those having sulfonic acid functionality, or weakly acidic cation exchangers such as those having carboxylic acid functionality. The average particle size of the commercially available forms of the resins is about 40 to 150 microns. The particle size of the resin is critical for topically administrable ophthalmic compositions. Accordingly, for topically administrable ophthalmic compositions, commercially available resin particles are reduced by known techniques, including grinding, ball milling and microfluidization, to a particle size of about 20 $\mu$m or less, such that the average particle size is $\leqq$ 10 $\mu$m. Preferably, the resin particles are reduced to a particle size of about 10 $\mu$m or less. Ion exchange resins are typically used in an amount from about 0.05 to about 10% (w/w), preferably a 1:1 ratio with the basic active.

Without being bound to any theory, it is believed that the release of the basic active held by the cation exchange resin and the anionic polymer is achieved when ions naturally present in the tear fluid, principally sodium and potassium, compete with the bound basic active for sites on the polymer vehicle and the ion exchange resin. Thus released, the basic active is presented to the eye surface for transport to the receptor sites.

Any pharmaceutical grade poly(styrenedivinyl benzene) cationic ion exchange resin having a degree of cross-linking, from about 4 to about 4.5% is suitable for the formulation, and can be used either in the hydrogen form or sodium form. Such resins are available, for example, from Rohm & Haas as Amberlite IR-118H (4.5% cross-linking) or Amberlyst 131 (4% cross-linking).

The compositions of the present invention can also include other components, for example, pharmaceutically acceptable buffers; tonicity agents; comfort-enhancing agents; solubilizing aids; pH-adjusting agents; antioxidants; preservatives and stabilizing agents. Suitable preservatives include: benzalkonium chloride, thimerosal, chlorobutanol, methyl paraben, propyl paraben, phenyl-ethyl alcohol, edetate disodium, sorbic acid, polyquatemium-1 and other agents known to those skilled in the art. Typically such preservatives are employed at a level of from 0.001 to 1.0% by weight. The tonicity, or osmolality, of the product can be adjusted to either hypotonicity, isotonicity or hypertonicity relative to normal tears by use of conventional materials known to the art. Such tonicity agents, however are limited to nonionic compounds and typically, when employed, range from 0.01 to 10% by weight in the final product. Nonionic agents include mannitol, dextrose, glycerine and propyleneglycol.

Formulation

Representative compounding procedures for gels and pourable liquids include the following.

1. Gels

The cationic exchange resin component is dispersed in water. The basic active component is then added with stirring. The polyanionic polymer component is then added. The resulting product has a viscosity ranging from 1000 to 300,000 cps depending on the anionic polymer concentration. The resulting pH is 3.0 to 8.5, which may be adjusted, if necessary, with HCl or other pH adjusting agent. The preservative pH is from 6.0 to 8.5.

2. Pourable Liquids

The cationic exchange resin component is dispersed in 10 to 50 vol. percent of total water taken in formulation, and then basic active is dispersed and/or dissolved with stirring. The polyanionic polymer, as an aqueous dispersion, is added until the desired pH of the product is obtained. The pH of the product can be adjusted to the desired value by varying basic active/polymer/resin ratio. If desired, final pH of product can be adjusted with addition of either NaOH or HCl or other pH adjusting agent. The preferred pH range for ophthalmic formulations is from 5.0 to 8.5. The final product is a dispersion, which may require high energy mixing to break any agglomeration to achieve uniformity. Other formulation ingredients are then added with mixing. The resulting product has a viscosity ranging from 1.0 to 20,000 cps depending on the anionic polymer concentration.

The ophthalmic formulations of the present invention are preferably administered topically to the eye. Typically, topical administration is necessary once or twice per day. The precise dosage regimen is left to the routine discretion of the clinician.

The following examples are intended to illustrate, but not limit, the present invention.

EXAMPLE 1

| INGREDIENT | A (0.25%) (w/w) | B (0.5%) (w/w) |
| --- | --- | --- |
| Betaxolol HCl | 0.28* | 0.56** |
| Resin | 0.25 | 0.5 |
| Carbomer 974P | 0.2 | 0.2 |
| Edetate Disodium | 0.01 | 0.01 |
| Mannitol | 4.5 | 4.5 |
| Benzalkonium Chloride | 0.01 | 0.01 |
| NaOH | q.s. to pH | q.s. to pH |
| Purified Water | q.s. to 100 | q.s. to 100 |

Resin prepared by grinding (pestle-mortar) to a mean particle size around 250 $\mu$m, the resin was then microfluidized for 10, 20, and 30 min at 15000 psi to obtain a mean particle size of 5 $\mu$m.
\* = 0.25% betaxolol
\*\* = 0.50% betaxolol

EXAMPLE 2

The Controlled Release Assay System (CRAS) described by Stevens et al., Analytical Chemistry 64:715–723 (1992), was used to estimate the release profile of betaxolol from sized resins with different cross-linking densities in the presence and absence of benzalkonium chloride. The same in vitro assay technique was used to estimate the release of betaxolol from full formulations made with microfluidized IR-118 and IRP-69. The data are summarized below:

| Amberlite | t1/2 (h) | % Bound | t1/2 (h) | % Bound | Betaxolol:Resin in t1/2 (h) | % Bound |
| --- | --- | --- | --- | --- | --- | --- |
| IR-118H (4.5%)* | 0.37 ± 0.06 | 86 | 0.65 ± 0.08 | 84 | 0.44 ± 0.12 | 91 |
| IRP-69 (8%)* | 0.24 ± 0.01 | 83 | — | 83 | 0.31 ± 0.04 | 86 |
| IR-122 (10%) | 0.44 ± 0.11 | 49 | — | 45 | — | 13 |
| 200 (20%) | 0.23 ± 0.06 | 3 | 0.49 ± 0.15 | 4 | — | — |

*Numbers in parenthesis represent percent cross-linking, with divinylbenzene.

Release of betaxolol from IR-118 suggests a more sustained action than from IRP-69 both in the presence and absence of formulation components. The lower cross-linking density of IR-118 results in larger pores for greater accessibility of betaxolol to internal binding sites; this also implies that, once released from their binding sites, betaxolol molecules will easily pass back through the larger pores into the solvent. It is expected, therefore, that as the cross-linking density of resin increases, betaxolol binding will be less and release will be slower. Contrary to this expectation, the observed release rate of betaxolol from IR-118 is slower than from IRP-69. This gives Amberlite IR-118 the edge over IRP-69 not only in terms of binding efficiency but also in terms of providing a more sustained release.

Procedure:

Finely divided resin and the basic active (betaxolol) are mixed at a 1:1 ratio in 50% of the total water volume component to form a uniform dispersion. After mixing (magnetic stirrer) at room temperature for approximately 2 hours, the Carbopol 974P is added slowly as an aqueous dispersion. The other ingredients are then added as aqueous solutions and the volume adjusted with water to obtain a white uniform suspension.

The invention has been described herein with reference to certain preferred embodiments. However, as obvious variations thereon will become apparent to those skilled in the art, the invention is not to be considered as limited thereto.

What is claimed is:

1. In a topically administrable aqueous ophthalmic composition comprising a basic active, a polyanionic polymer and a cation exchange resin, the improvement wherein the cationic exchange resin consists essentially of a poly(styrenedivinyl) benzene cation exchange resin having a degree of cross-linking from about 4 to about 4.5%.

2. The composition of claim 1 wherein the basic active is an ophthalmically acceptable beta blocker.

3. The composition of claim 2 wherein the beta blocker has the structure

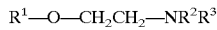

wherein:

$R^1$ is a substituted or unsubstituted cyclic or aliphatic moiety; and $R^2$ and $R^3$ are independently selected from H and substituted and unsubstituted alkyl.

4. The composition of claim 3 wherein the beta blocker is selected from the group consisting of betaxolol; timolol; befunolol; labetalol; propanolol; bupranolol; metaprolol; bunalol; esmalol; pindolol; carteolol; hepunolol; metipranolol; celiprolol; azotimolol; diacetolol; acebutolol; salbutamol; atenulol; and isoxaprolol.

5. The composition of claim 4 wherein the beta blocker is selected from the group consisting of betaxolol and timolol.

6. The composition of claim 1 wherein the basic active is present in an amount of from about 0.01 to 4.0 wt. %.

7. The composition of claim 6 wherein the basic active is present in an amount of from about 0.10 to 1.0 wt. %.

8. The composition of claim 1 wherein the polyanionic polymer comprises carboxylic acid functional groups containing from 2 to 7 carbon atoms per carboxylic acid functional group.

9. The composition of claim 8 wherein the polyanionic polymer is a carboxy vinyl polymer.

10. The composition of claim 1 wherein the polyanionic polymer is present in an amount of from about 0.05 to 8 wt. %.

11. The composition of claim 1 wherein the cationic exchange resin is present in an amount of from about 0.05 to 10 wt. %.

12. The composition of claim 11 wherein the cationic exchange resin is present in an amount equal to about a 1:1 ratio with the basic active.

13. The composition of claim 1 wherein the cationic exchange resin is a poly(styrenedivinyl) benzene cation exchange resin having a degree of cross-linking of about 4%.

14. The composition of claim 1 wherein the cationic exchange resin is a poly(styrenedivinyl) benzene cation exchange resin having a degree of cross-linking of about 4.5%.

15. The composition of claim 1 wherein the composition further comprises one or more components selected from the group consisting of pharmaceutically acceptable buffers; nonionic tonicity agents; comfort-enhancing agents; solubilizing aids; pH-adjusting agents; antioxidants; preservatives and stabilizing agents.

* * * * *